(12) United States Patent
Clawson

(10) Patent No.: US 6,607,481 B1
(45) Date of Patent: Aug. 19, 2003

(54) METHOD AND SYSTEM FOR AN IMPROVED ENTRY PROCESS OF AN EMERGENCY MEDICAL DISPATCH SYSTEM

(76) Inventor: Jeffrey J. Clawson, 4649 Farm Meadow La., Salt Lake City, UT (US) 84117

(*) Notice: Subject to any disclaimer, the term of this patent is extended or adjusted under 35 U.S.C. 154(b) by 0 days.

(21) Appl. No.: 09/689,986

(22) Filed: Oct. 10, 2000

(51) Int. Cl.$^7$ .......................... A61B 5/00; H04M 11/04
(52) U.S. Cl. ................. 600/300; 128/897; 128/903; 705/2; 379/38
(58) Field of Search ................. 600/300, 301, 600/486, 529; 128/903, 904, 920–925; 705/2–4, 9; 455/404; 702/19; 707/10, 104.1; 296/19, 20; 379/38–39, 45, 48–51, 106.1–106.2; 340/286.01, 286.06–286.07

(56) References Cited

U.S. PATENT DOCUMENTS

| | | |
|---|---|---|
| 3,799,147 A | 3/1974 | Adolph et al. |
| 4,290,114 A | 9/1981 | Sinay |
| 4,360,345 A | 11/1982 | Hon |
| 4,731,725 A | 3/1988 | Suto et al. |
| 4,922,514 A | 5/1990 | Bergeron et al. |
| 5,086,391 A | 2/1992 | Chambers |
| 5,228,449 A | 7/1993 | Christ et al. |
| 5,339,351 A | 8/1994 | Hoskinson et al. |
| 5,348,008 A | 9/1994 | Bornn et al. |
| 5,404,292 A | 4/1995 | Hendrickson |
| 5,438,996 A | 8/1995 | Kemper et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,660,176 A | 8/1997 | Iliff |
| 5,722,418 A | 3/1998 | Bro |
| 5,724,983 A | 3/1998 | Selker et al. |
| 5,759,044 A | 6/1998 | Redmond |
| 5,761,493 A | 6/1998 | Blakeley et al. |
| 5,805,670 A | 9/1998 | Pons et al. |
| 5,809,493 A | 9/1998 | Ahamed et al. |
| 5,826,077 A | 10/1998 | Blakeley et al. |
| 5,844,817 A | 12/1998 | Lobley et al. |
| 5,857,966 A | 1/1999 | Clawson |
| 5,910,987 A | 6/1999 | Ginter et al. |
| 5,915,019 A | 6/1999 | Ginter et al. |
| 5,926,526 A | 7/1999 | Rapaport et al. |

(List continued on next page.)

Primary Examiner—Max F. Hindenburg
Assistant Examiner—Michael Astorino
(74) Attorney, Agent, or Firm—Lloyd W. Sadler

(57) ABSTRACT

An improved method and system for receiving, processing and responding to emergency medical calls by emergency dispatchers is described. A consistent, standard and systematic process is provided which in combination with adequate training, supervision and quality assurance serves to provide a method for gathering emergency medical information, categorizing such information into various determinant levels for appropriate response, and for giving qualified emergency medical information to callers thereby permitting "zero-time" response by those at the scene. By using this invention properly a dispatcher is guided through the interrogation of callers, gathering the critical information, dispatching the appropriate mobile care rapidly when needed and giving the appropriate guidance to the caller. This invention specifically guides the dispatcher through the universal entry protocol, paying particular attention to medical complaints related to respiratory arrest.

5 Claims, 6 Drawing Sheets

U.S. PATENT DOCUMENTS

| | | |
|---|---|---|
| 5,962,891 A | 10/1999 | Arai |
| 5,964,700 A | 10/1999 | Tallman et al. |
| 5,989,187 A | 11/1999 | Clawson |
| 5,991,751 A | 11/1999 | Rivette et al. |
| 6,004,266 A | 12/1999 | Clawson |
| 6,010,451 A | 1/2000 | Clawson |
| 6,022,315 A * | 2/2000 | Iliff ............................ 600/300 |
| 6,035,187 A | 3/2000 | Franza |
| 6,053,864 A | 4/2000 | Clawson |
| 6,074,345 A | 6/2000 | van Oostrom et al. |
| 6,076,065 A | 6/2000 | Clawson |
| 6,078,894 A | 6/2000 | Clawson et al. |
| 6,106,459 A | 8/2000 | Clawson |
| 6,115,646 A | 9/2000 | Fiszman et al. |
| 6,117,073 A | 9/2000 | Jones et al. |

* cited by examiner

ENTRY QUESTIONS

1. What's the address of the emergency?
2. What's the phone number you're calling from?
3. What's the problem, tell me exactly what happened?
   Hanging      ☠ 9-E-3
   Underwater      ☠ 9-E-6 a. (Not obvious) Are you with patient now?
   b. (Not obvious) How many people are hurt (sick)? ___
      Traffic accident      29
      Multiple victims      CC
   c. (Choking) Is s/he still choking now? (You go check and tell me what you find.) ☠ 11-E-1

4. How old is s/he?
   a. (Unsure) Tell me approximately. then.

5. Is s/he conscious?
   Yes
   No ✓
   Unknown

5. Is s/he breathing?
   a. (Hasn't checked-2nd party caller) You go check and tell me what you find.
   Yes
   No/NOT BREATHING      ☠ ?-E-?
   Uncertain/INEFFECTIVE BREATHING (2nd party)      ☠ ?-E-?
   Unknown (3rd or 4th party caller)

---

THE NATIONAL ACADEMY
EMD PROTOCOL
medical priority dispatch system

CRITICAL EMD INFORMATION

* For NOT BREATHING situations or INEFFECTIVE BREATHING, code as ECHO on Protocols 2,6,9,11,15,31 only, initiate dispatch, give PDIs, and return to question sequence when directed by ☠ symbol.

POST-DISPATCH INSTRUCTIONS a. (ECHO) I'm sending the paramedics (ambulance) to help you now. Stay on the line.
b. (Hanging and not OBVIOUS DEATH) Cut her/him down immediately and see if s/he's breathing. (Loosen noose first.)
c. (Underwater) Do not go in the water unless it is safe to do so. ✓
d. (Critical Caller Danger) If it's too dangerous to stay where you are, and you think you can leave safely, get away and call me from somewhere safe. ✓

NOT BREATHING Situations

The following, when offered in response to "What's the problem" or any listed Entry Question:

| | |
|---|---|
| • Choking (verified) | 11-E-1 |
| • Not breathing at all | 9-E-1 |
| • Breathing uncertain (agonal) | 9-E-2 |
| • Hanging | 9-E-3 |
| • Strangulation | 9-E-4 |
| • Suffocation | 9-E-5 |
| • Underwater | 9-E-6 |

INEFFECTIVE BREATHING

The following, when volunteered at any point during Case Entry (code as ECHO on 2,6,9,11,15,31):
- "Barely breathing"
- "Can't breathe at all"
- "Fighting for air"
- "Gasping for air" (agonal respirations)
- "Making funny noises" (agonal respirations)
- "Not breathing"
- "Turning blue or purple"

ECHO Determine Practice

The ECHO level allows early recognition and closer response initiation based on extreme conditions of breathing. Such coding is separated from DELTA to encourage local assignment of the absolute closest response of any trained crew (i.e., police with AEDs, fire ladder or snorkel crews, HAZMAT or other specialty teams).

OBVIOUS DEATH (See definition and authorizations on Protocol 9, A1.)

Rules

1. If the Chief Complaint includes scene safety issues, choose the protocol that best addresses those issues.
2. If the Chief Complaint involves TRAUMA, choose the protocol that best addresses the mechanism of injury.
3. If the Chief Complaint appears to be MEDICAL in nature, choose the protocol that best fits the patient's foremost symptom, with priority symptoms taking precedence.
4. Case Entry questioning must always be completed, even when an ECHO determinant has been selected.
5. Chief Complaint key questioning must always be completed to cover scene safety issues, even when an ECHO determinant is selected.
6. If the Chief Complaint and status of consciousness and breathing are unknown initially (3rd party caller), go to Protocol 32.
7. If traffic/transportation accident, determine the number of patients, then go to Protocol 29.
8. The patient's age does not need to be determined initially in multiple-patient events. If individual patient assessment is possible, age should be determined.
9. When the initial Chief Complaint appears to be seizure, go to Protocol 12 regardless of consciousness and breathing status.
10. Ask, "Is the patient male or female?" if the patient's gender is not obvious.
11. Do not advise callers to perform any PDIs or PAIs until all safety key questions are completed (those in red).

Axioms

1. Uncertain breathing status indicates a 2nd party caller who has seen the patient and is still unsure. This is considered NOT BREATHING until proven otherwise.
2. Unknown breathing status indicates a 3rd or 4th party caller who cannot personally verify the patient's status.
3. after an ECHO response, completing all Case Entry and Chief Complaint key questions ensures that the proper knowledge regarding safety issues and the appropriate warnings and/or advice are immediately and always passed on to the responders and potential scene helpers.

❶ CASE ENTRY PROTOCOL

FIG. 7b

METHOD AND SYSTEM FOR AN IMPROVED ENTRY PROCESS OF AN EMERGENCY MEDICAL DISPATCH SYSTEM

BACKGROUND OF THE INVENTION

1. Field of the Invention

This invention relates to methods and systems for processing and responding to emergency medical inquiries. Specifically, this invention relates to the process or method for receiving and processing critical information regarding emergency medical calls. Also, this invention specifically relates to a system and apparatus for performing the steps of a process for receiving and processing critical emergency medical information.

Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing a consistent and proven system for: First, gathering necessary medical complaint information from emergency medical inquiry callers. Second, prioritizing the complaint to determine the criticality of the emergency. Third, providing emergency verbal instructions to individuals at the scene. Fourth, assisting dispatched responders to be prepared for each emergency situation. And, fifth, advising those on the way to provide care at the scene of specific problems or potential hazards. When used correctly this invention decreases the effective response time, while increasing the professionalism and control of emergency medical dispatchers; increases the accuracy and appropriateness of patient interrogation and well as the quality of gathered information; reduces the number of multiple unit and light-and-siren responses thereby reducing the risk of emergency medical vehicular collisions; improves patient care; reduces burn-out and stress of dispatchers by improving their quality of training and performance; decreases the risk of responder injury or mistake by providing responders with improved knowledge of the situation; and provides a means for continuously improving the quality of emergency medical dispatching and, as a result, emergency patient care.

2. Description of Related Art

It is desirable to provide a systematic and standardized method for responding to emergency medical requests. Although in the related art some attempt has been made to address the problem of medical care assessment, the related art does not address the specific problems of emergency dispatcher response. Rather related art approaches known to the applicant describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility. Also, several patents issued to the inventor of this invention are directed to several specific issues of an emergency medical dispatch system, but do not describe the specific improvements and entry process steps of this invention.

For general background material, the reader is directed to U.S. Pat. Nos. 3,799,147, 4,130,881, 4,237,344, 4,290,114, 4,360,345, 4,489,387, 4,731,725, 4,839,822, 4,858,121, 4,922,514, 4,945,476, 5,063,522, 5,065,315, 5,072,383, 5,086,391, 5,228,449, 5,253,164, 5,255,187, 5,339,351, 5,348,008, 5,404,292, 5,438,996, 5,462,051, 5,471,382, 5,502,726, 5,513,993, 5,516,702, 5,521,812, 5,544,649, 5,554,031, 5,590,269, 5,594,638, 5,596,994, 5,660,176, 5,722,418, 5,724,983, 5,759,044 5,761,493, 5,805,670, 5,809,493, 5,826,077, 5,844,817, 5,857,966, 5,910,987, 5,915,019, 5,926,526, 5,964,700, 5,962,891, 5,989,187, 5,991,751, 6,004,266, 6,010,451, 6,035,187, 6,053,864, 6,074,345, 6,076,065, 6,078,894, 6,106,459, 6,115,646, and 6,117,073. Each of the above references is hereby incorporated by reference in its entirety for the material disclosed therein.

SUMMARY OF THE INVENTION

It is desirable to provide an improved system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such. responders with increased safety awareness and knowledge of the field situation.

Accordingly, it is the primary object of this invention to provide a medical dispatch system that is designed to programmatically guide the medical dispatcher through the initial interrogation, obtaining all critical patient information.

A further object of this invention is to provide a method and system which produces a determinate value, establishing the criticality of the call as well as defining the appropriate response, based, at least partially, on the responses to the programmed initial interrogation, that is upon the critical patient information.

Another object of this invention is to provide a cross-referenced scripted set of instructions to be given by the dispatcher to the caller in a medical emergency situation.

It is a further object of this invention to provide a method of determining the criticality of a medical emergency and communicating such level of criticality to the response personnel.

It is a still further object of this invention to provide a method for gathering and communicating information concerning the situation at the field location to the response personnel and the emergency medical callers.

A further object of this invention is to improve the quality, efficiency and usefulness of the information received to and communicated by emergency medical dispatchers thereby improving the quality of emergency medical services provided to patient before, during and after the arrival of emergency medical technicians.

A still further object of this invention is to provide a method, system and apparatus for an improved entry protocol for emergency medical dispatchers.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross-referenced cards with scripted questions, instructions and categorizations is provided. Second, a computerized process is provided with software controlling the access and reference points to a computerized database of emergency medical inquiries and instructions are provided. Each preferred embodiment incorporates the same essential method of this invention, though each has its own particular advantages.

BRIEF DESCRIPTION OF THE DRAWINGS

FIGS. 7a and 7b depict the preferred embodiment of the flip cards showing the steps of the entry protocol of the flip card deck embodiment of the invention.

Reference will now be made in detail to the present preferred embodiment of the invention, examples of which are illustrated in the accompanying drawings.

DETAILED DESCRIPTION OF THE INVENTION

This invention provides a method, system and an apparatus for receiving, processing and communicating emergency medical information, enabling an assessment of the critical or "key" information by trained emergency medical dispatch personnel. When the invention is properly employed the initial interrogation of the caller or patient will provide critical patient information, such as the patient's location, the caller's phone number, a description of what happened, the number of people hurt, injured or sick, the patient's age, and the patient's status as to consciousness and breathing. This information is then immediately put to use identifying the criticality of the emergency and the appropriate medical response, as well as leading to a series of established medical instructions for the dispatcher to give to the caller.

Figure 1:
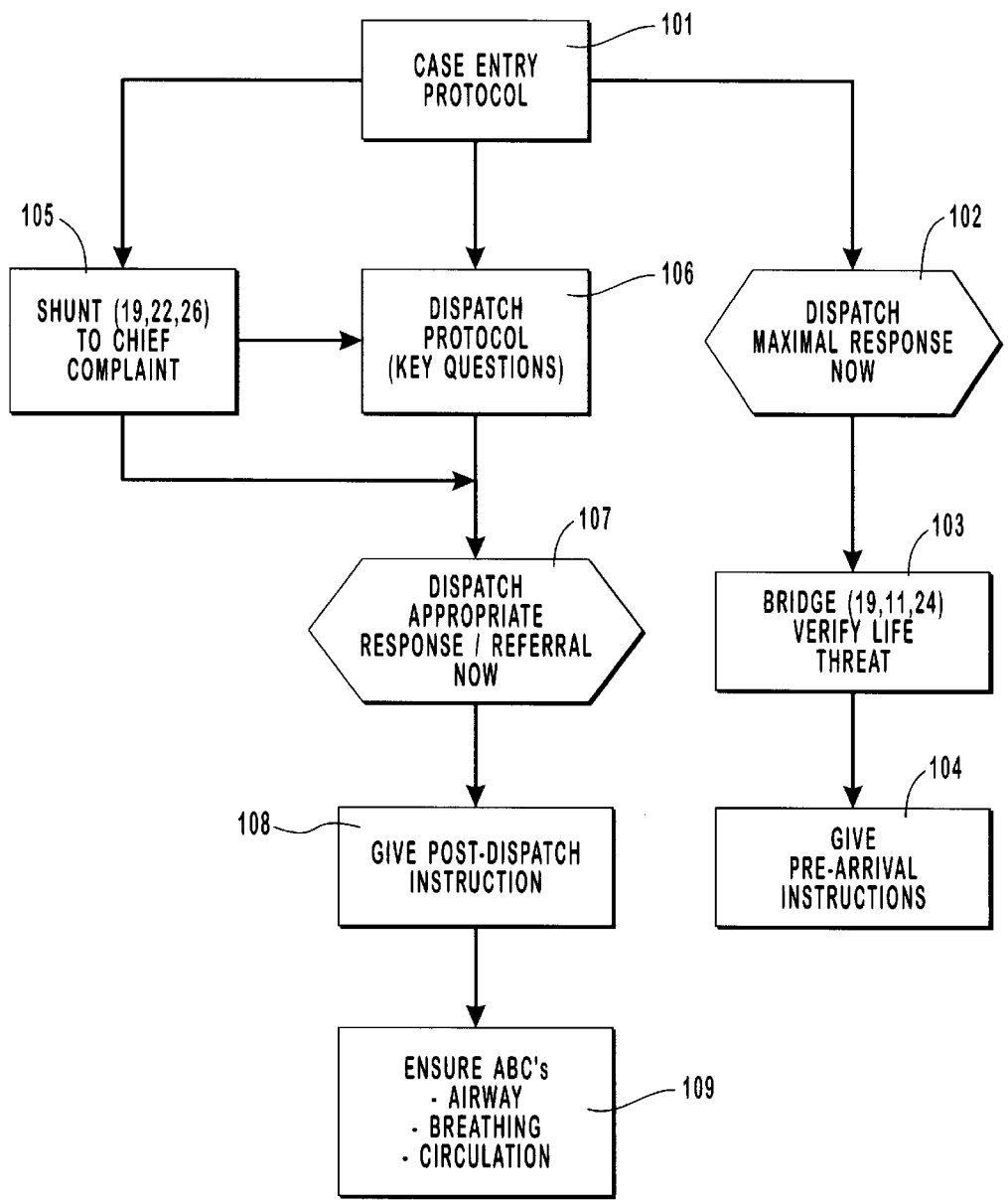
FIG. 1 depicts the principle elements of the complete system in which the preferred embodiment of the invention operates and the relationship of the elements of the system to each other and puts into the context of the complete system, the specific claimed invention.

FIG. 1 shows the complete system in which the invention operates in its best mode. The process of managing emergency medical dispatchers, the information they require and the information they give is detailed in FIG. 1. The case entry protocol 101, the heart of this invention, provides the initial steps through which the all emergency callers or patients are taken to provide symptom information and to access medical information. The purpose of the case entry protocol 101 is to receive sufficient information to permit the dispatcher to identify the caller's chief complaint. This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. The life threat is then verified 103 and pre-arrival instructions are given 104. These pre-arrival instructions 104 include six treatment sequence algorithmic scripts covering Arrest, Choking, and Childbirth. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the five levels (Alpha—A, Bravo—B, Charlie—C, Delta—D, Echo—E) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
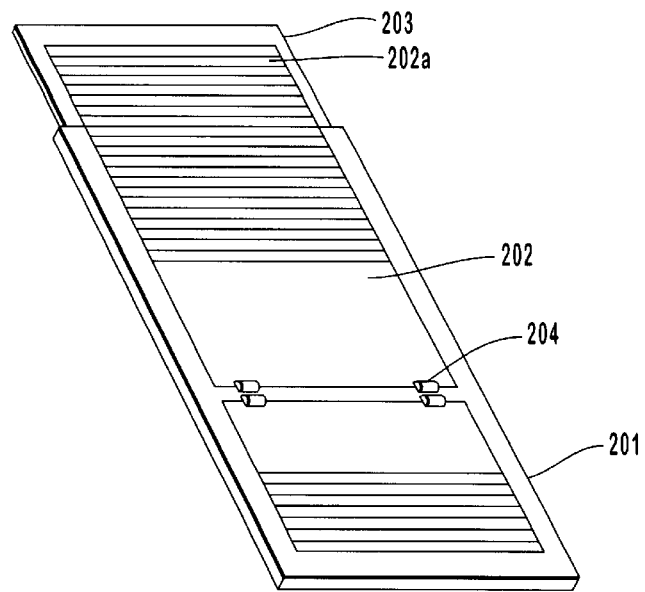
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202a. Alternative embodiments of the card apparatus can be a deck of cards bound in a manner well known to those skilled in the art. In a present embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision-making process.

Figure 3:
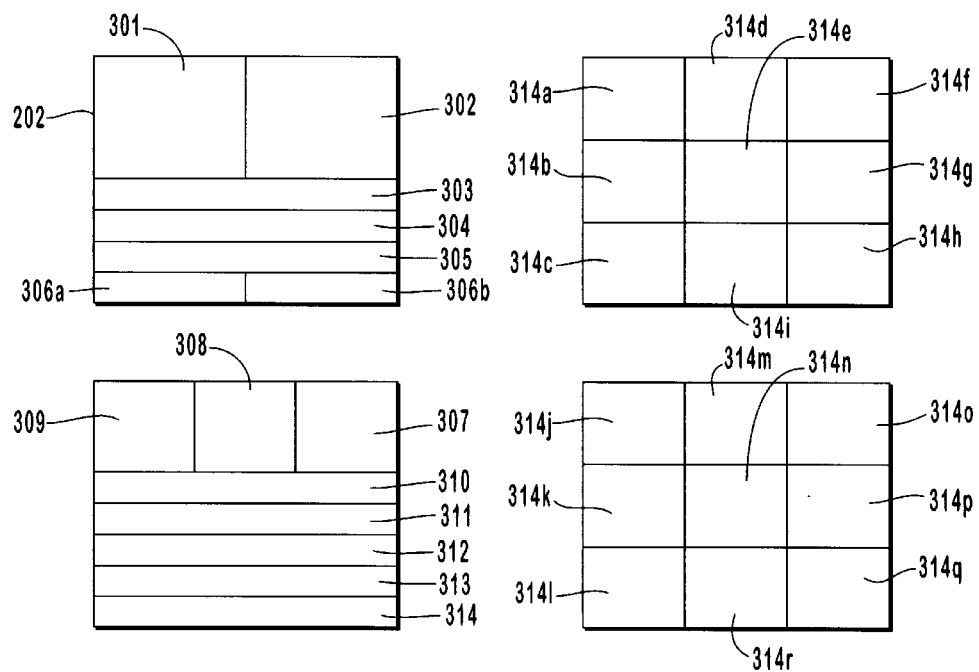
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A—Alpha 303, B—Bravo 304, C—Charlie 305, D—Delta 306a or E—Echo 306b are provided to aid the dispatcher in making the determinant designation. Each determinant level may have one or more sublevels. Generally, the most critical call is given a determinant level of E—Echo, with D—Delta nearly as critical, and the least critical call is given a determinant level of A—Alpha. The more critical the determinant level assigned to a call, the more medical resources and urgency may be applied to provide help. For example, an A—Alpha call will typically be responded to by emergency medical technicians and an ambulance proceeding to the patient under the safest method reasonably possible, while a D—Delta call will typically be responded to by the closest emergency medical technicians, an ambulance, paramedics, all who will proceed under the most urgent method possible. Sublevels may not indicate the criticality of the call; rather sublevel designations indicate the type of call, information often especially important to the dispatched medical team. After the determinant code is determined 303–306a,b the dispatcher is referred to the post-dispatch instructions section 302. The purpose of the post-dispatch instructions is to systematically prepare for and expedite the field personnel's job at the scene, and prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314a–r. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306a,b, and the post-dispatch instructions of section 302 into context for the dispatcher.

Figure 4A:
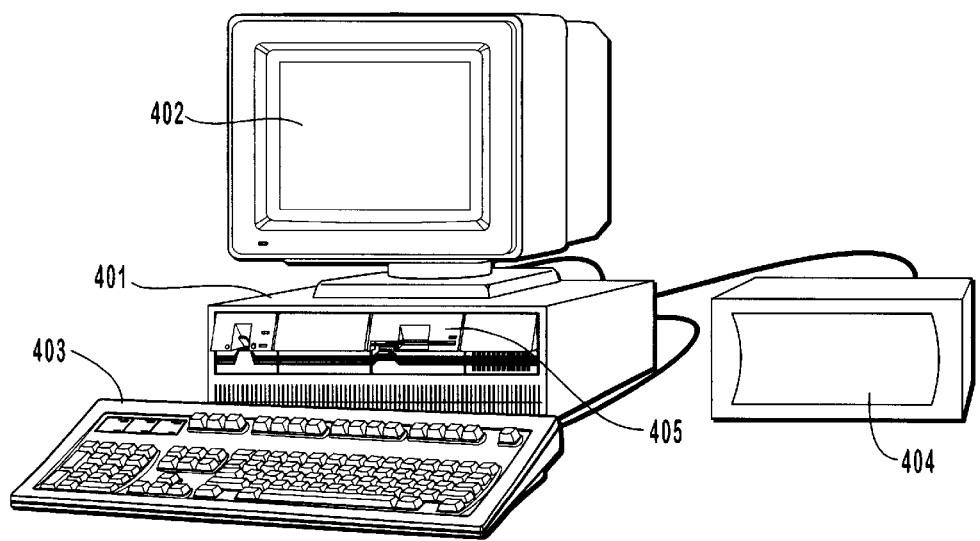
FIGS. 4a and 4b show system components of a typical computer system and telephone communication system used in the preferred embodiment of the invention.
Figure 4B:
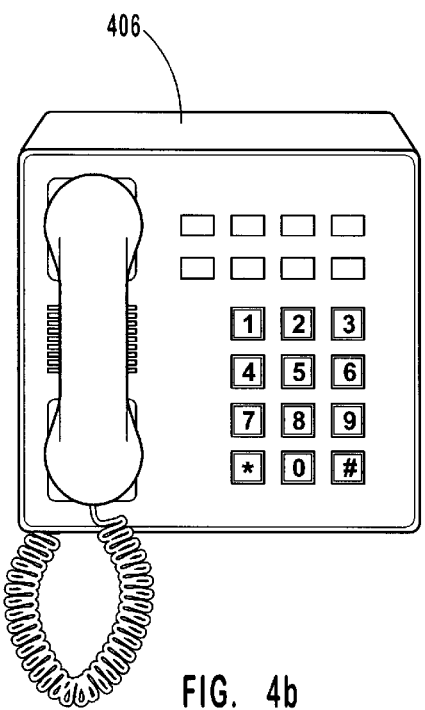

FIG. 4a shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information. FIG. 4b shows the typical telephone communication device as used with this invention to communicate between the dispatcher and emergency medical callers and/or paramedics (or EMTs).

Figure 5:
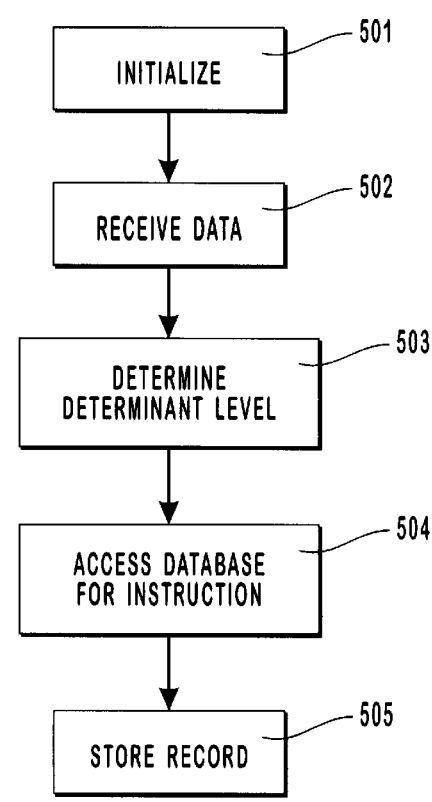
FIG. 5 shows a flow chart representation of the preferred top-level steps of the invention.

FIG. 5 shows a process flow chart representation of the preferred top-level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A database is accessed 504 to produce the appropriate instructions for communication with the caller. Records of the calls and queries are stored 505, for historical reports, for review of the dispatchers and for continued quality assurance control.

Figure 6:
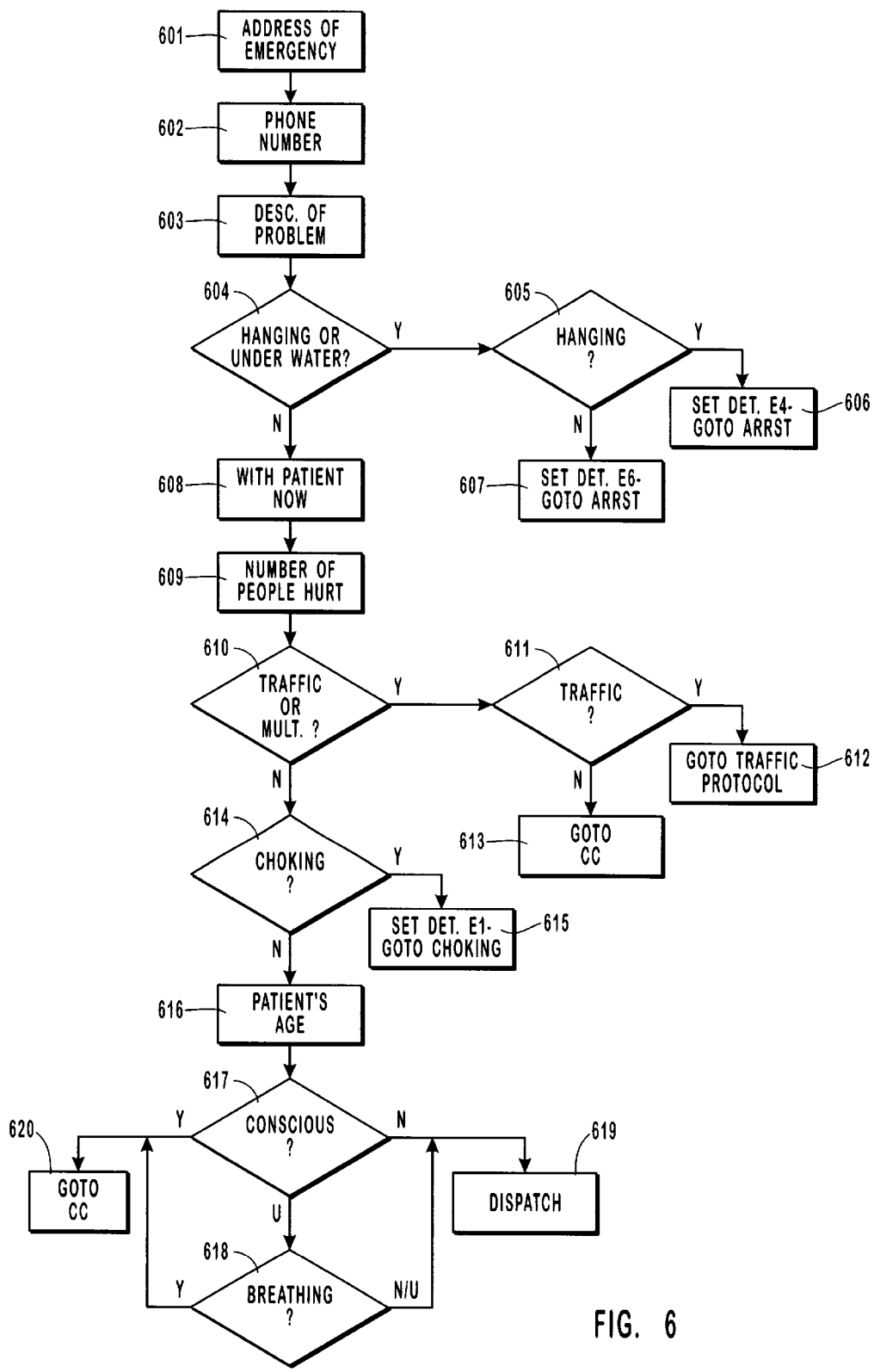
FIG. 6 depicts the detailed steps of the entry protocol steps of the process of the preferred embodiment of the invention.

FIG. 6 depicts the detailed steps of the entry protocol process of the preferred embodiment of the invention. The following steps of the process of the invention need not be accomplished in this specific order, alternative ordering of the steps of the invention are possible. This order of the steps of the process has been determined by the inventor to be the best mode of the invention. First, the address of the emergency is determined 601. This address or location is clearly essential if the dispatch of a response team is necessary. Next, the phone number where the caller is calling from is learned 602. Having the caller's phone number permits the dispatcher to call back if the call is prematurely disconnected, or if there is difficulty locating the scene or the patient. A description of the chief complaint or problem is then acquired 603 from the caller. The chief complaint, which is the reason the patient is seeking medical care, must contain sufficient information to allow the categorization of the problem into one of thirty-two defined, chief complaints. Such categorization permits the dispatcher to branch to a protocol designed specifically to respond to the patient's specific problem. If the description of the problem learned in step 603 involves a person who is hanging or was found underwater 604, whether hanging or underwater is determined 605 and the determinate is set to E-6 606, 607 and the dispatcher immediately proceeds to the Arrest Protocol. The Arrest Protocol is critical in these situations because a person suffering from respiratory arrest almost certainly requires the most immediate medical care possible. If the patient was not hanging or found underwater, the inquiry is made as to whether the caller is with the patient now 608. Next, the dispatcher learns the number of people involved or injured 609. An inquiry 610 is made as to whether the injury was caused by a traffic accident, or if a multiple number of victims are involved. If the injury was caused by a traffic accident 611, the dispatcher is immediately branched to the traffic accident protocol 612. If it is not a traffic accident, but multiple victims are involved, the dispatcher goes to the Chief Complaint 613 for additional information. If the injury involves only one person and was not caused by a traffic accident, then the dispatcher learns if the patient is choking 614. If the patient is choking, then the determinate is set to E-1 and the dispatcher immediately proceeds to the choking protocol 615. If the patient is not choking, the dispatcher learns the patient's age 616. Next, an inquiry is made as to whether the patient is conscious 617. If the patient is not conscious then the dispatcher immediately dispatches emergency medical assistance. If the caller is uncertain if the patient is conscious, the dispatcher further inquires as to whether the patient is breathing 618. If the caller is uncertain or believes the patient is not breathing, the dispatcher immediately dispatches emergency medical assistance. If the patient is conscious, the dispatcher continues with the interrogation based on the protocol associated with the Chief Complaint 620.

FIGS. 7a and 7b depict the preferred embodiment of the flip cards showing the steps of the entry protocol invention. The entry questions 701 (numbered 1–6) are shown in the Entry Questions section 702. Specific critical answers are shown 703, including "Hanging," "Underwater," "Traffic Accident," "Multiple Victims", as well as responses to the consciousness and breathing inquiries. The determinate and protocol assignments based on the critical answers 703 are provided in column 704. Critical information for the dispatcher is provided 705, as are post dispatch instructions 706 for the dispatcher to give is specific shown circumstances. Identification of Non Breathing Situations is provided in section 707 along with the protocol and criticality determinate assigned. For example, if the response to the question "What is the problem?" involves choking, the dispatcher assigns a criticality determinate of E-1 and jumps to the choking protocol. Section 708 provides a list of responses related to Ineffective Breathing, which if received, assigns a criticality of E—Echo. The Echo Determinate practice is described in section 709. An Obvious Death section 710 is provided to assist the dispatcher in situations where death of one or more patients is reported. An Axiom list 711 is provided to remind the dispatcher about considerations regarding uncertain or unknown breathing status, and to complete case entry process and the Chief Complaint protocol after an E—Echo determination even after dispatching an emergency medical response. This information is relayed to the paramedics or EMTs to assist them in performing their duties in the most efficient manner possible.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for managing the entry process of an emergency medical dispatch system, for dispatching medical assistance to persons needing such medical assistance, comprising the steps of:

（a) receiving a medical call on a telephone communication device regarding a patient needing medical assistance because of a health problem;

(b) receiving a description of the health problem giving rise to said call for medical assistance;

(c) identifying if the patient needing medical assistance is suffering ineffective breathing;

(d) determining a criticality value based on the description of said health problem;

(e) selecting an appropriate response, wherein such response depends on said described health problem, a received age, a determination of consciousness and a determination of breathing, and wherein said appropriate response includes an arrest protocol for patients in respiratory arrest;

(f) calculating a determinate value based on said described health problem, said received age, said determination of consciousness and said determination of breathing; and (g) dispatching, based on said calculated determinate value, an appropriate emergency medical response, wherein said emergency medical response is provided by field emergency medical care-givers.

2. A method as recited in claim 1, wherein said identifying if the patient needing medical assistance is in respiratory arrest further comprises determining if the patient was hanging or was underwater.

3. A method as recited in claim 1, further comprising the step of determining if the patient is choking.

4. A method as recited in claim 1, further comprising the step of determining the number of persons who are injured.

5. A method as recited in claim 1, further comprising the step of determining of the cause of the patient's injury was a traffic accident.

* * * * *